United States Patent [19]

Palmer et al.

[11] 3,975,450

[45] Aug. 17, 1976

[54] PROCESS FOR THE PREPARATION OF POLYHYDRIC ALCOHOLS

[75] Inventors: Billy W. Palmer; David L. Bondurant; Hugh J. Hagemeyer, Jr., all of Longview, Tex.

[73] Assignee: Eastman Kodak Company, Rochester, N.Y.

[22] Filed: Sept. 3, 1974

[21] Appl. No.: 502,331

[52] U.S. Cl............................ 260/635 P; 260/618 R
[51] Int. Cl.$^2$.......................................... C07C 29/00
[58] Field of Search................................... 260/635 P

[56] References Cited
UNITED STATES PATENTS 2,081,322   5/1937   Carney............................ 260/638 R 3,239,572   3/1966   Zinsstag........................... 260/638 R

FOREIGN PATENTS OR APPLICATIONS 958,654   5/1964   United Kingdom............ 260/635 P Primary Examiner—Joseph E. Evans
Attorney, Agent, or Firm—Edward R. Weber; Daniel B. Reece, III

[57] ABSTRACT

Polyhydric alcohols are prepared by the aldol condensation of an aldehyde having 1 to 3 hydrogens on the alpha-carbon atom with formaldehyde in the presence of sodium carbonate and the subsequent crossed Cannizzaro reaction wherein the aldol condensation product is reacted with additional formaldehyde and sodium carbonate to form a polyhydric alcohol.

11 Claims, No Drawings

PROCESS FOR THE PREPARATION OF POLYHYDRIC ALCOHOLS

It is known that polyhydric alcohols can be made by an aldol condensation in an alkaline medium followed by a crossed Cannizzaro reaction. The literature contains many examples of the base catalyzed aldol reaction of an aldehyde and formaldehyde in the presence of strongly basic materials such as calcium hydroxide and sodium hydroxide. No complete process using only sodium carbonate as the basic material has been described wherein both the aldol and crossed Cannizzaro reactions are conducted simultaneously. The mere substitution of sodium carbonate for sodium hydroxide or calcium hydroxide in the known processes would not be expected to be successful. The less basic catalyst produces a slower reaction and will frequently require a higher temperature to cause the reaction to proceed. The longer reaction time and higher temperature would be expected to result in the production of more undesirable by-products.

In the known processes using calcium or sodium hydroxide the product stream contains significant amounts of sodium or calcium salts. Prior to refining of the polyhydric alcohol these salts must be removed. Because of environmental considerations it is no longer feasible to merely discharge the removed salts as an effluent waste stream. The recovery and reuse of the salts, however, requires that they be recausticized which in itself produces waste products to be disposed of. When sodium carbonate can be used, the recovered salts may be reconverted to sodium carbonate by the application of heat and no waste disposal problem is incurred.

It is, therefore, an object of this invention to devise a process for the manufacture of polyhydric alcohols from an aldehyde and formaldehyde utilizing sodium carbonate.

A further object of the invention is to devise a continuous process for the manufacture of polyhydric alcohols.

Yet another object of the invention is to devise a continuous process for the production of polyhydric alcohols wherein the waste materials requiring disposal are kept to a minimum.

These and other objects of the invention will become apparent from the following description and the appended claims.

In the process of the invention an aldehyde having the formula $R_{3-n}H_nC-CHO$ is reacted with formaldehyde in the presence of sodium carbonate to form an aldol condensation product, which aldol condensation product is reacted with additional formaldehyde and sodium carbonate to form a polyhydric alcohol according to the following reaction:

<u>Aldol</u>

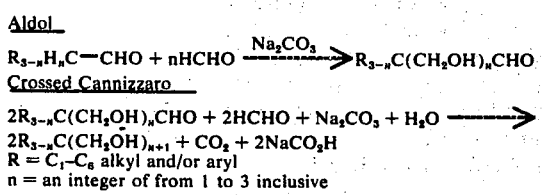

$R_{3-n}H_nC-CHO + nHCHO \xrightarrow{Na_2CO_3} R_{3-n}C(CH_2OH)_nCHO$

<u>Crossed Cannizzaro</u>

$2R_{3-n}C(CH_2OH)_nCHO + 2HCHO + Na_2CO_3 + H_2O \longrightarrow$
$2R_{3-n}C(CH_2OH)_{n+1} + CO_2 + 2NaCO_2H$
$R = C_1-C_6$ alkyl and/or aryl
$n$ = an integer of from 1 to 3 inclusive The reaction may be conducted in either a batch-type process or in a continuous fashion. A complicating factor in operating the reactor in a continuous fashion is the formation of sugar-like compounds by the base catalyzed self-condensation of formaldehyde. The formation of these sugars is autocatalytic and upon further heating causes the formation of a black color. After the aqueous solution turns black, sugar formation becomes the predominant reaction and no more formaldehyde will react to produce the desired polyhydric alcohol. Another factor involved is the removal of carbon dioxide as it is formed. If excess sodium carbonate is added the basicity of the reaction medium does not increase unless the solution is degassed to remove carbon dioxide which acts as an acid according to the following equation:

$Na_2CO_3 + H_2O + CO_2 \rightleftharpoons 2NaHCO_3$

In one embodiment of the invention an aqueous solution of an aldehyde, formaldehyde, and sodium carbonate is fed into a backmix continuously stirred reactor. The temperature and residence time in this reactor are adjusted so that 85 to 90 percent of the available formaldehyde and sodium carbonate are reacted. The effluent from this reactor is conducted to a distillation column which acts as a second reactor. The temperature of the first reactor may be altered as desired so long as the residence time is adjusted so that from 10 to 15 percent of the available formaldehyde remains unreacted. The practical lower limit is that temperature wherein excessive time is required to attain 85% utilization of the formaldehyde. The effective upper limit is the boiling point of the reactant solution at the pressure being utilized. Essentially all the higher aldehyde must be reacted with the formaldehyde in this first stage reaction. If the reaction is not carried to the point where at least 85% of the formaldehyde is reacted, there will probably be unreacted higher aldehyde. This in turn will result in a lower yield as the formaldehyde in the second stage will not have sufficient aldol to react with. If the reaction is carried to a higher conversion in this first stage, the reaction medium rapidly darkens and conversion of the higher aldehyde to the desired polyhydric alcohol product rapidly decreases. This decrease is accompanied by the formation of undesirable by-products.

In the distillation column, which operates as a secondary reactor, the remaining unreacted aldol condensation product is converted to the desired polyhydric alcohol. The elevated temperatures and active boiling in the distillation column serve to degas the reaction so that only a slight excess of sodium carbonate is required. In the base of the distillation column all excess formaldehyde is consumed. The distillation column is operated under essentially total reflux. However, if desired, any low boiling materials such as methyl alcohol and $\alpha$-ethyl acrolein which are produced may be removed by a small purge stream. Residence time in the base of the distillation column is unimportant so long as all the formaldehyde contained therein is reacted. The temperatures are selected so that active boiling occurs in the base of the column and that any low boiling compounds formed are removed from the top of the column as a vapor. Operating under these conditions, normal residence time will be from one-half to 1 hour. Minimum time is that time necessary to assure that all of the formaldehyde is reacted. The maximum time is determined solely by the size of the equipment.

In order to more clearly exemplify this novel invention the following description of a specific embodiment is provided wherein isobutyraldehyde and formaldehyde are reacted to form neopentyl glycol. Isobutyraldehyde, formaldehyde (as 37% formalin) and a 20% aqueous sodium carbonate solution are fed continuously to a back mix continuously stirred reaction in a ratio of 1.0:2.01:0.55, respectively. Temperature and residence time in this first vessel are adjusted so that 85–90% of the available formaldehyde and sodium carbonate are reacted.

A useful range for the temperature of the reaction mixture in the first reaction vessel has been found to be from about 50°C. to about 110°C. when the reaction is conducted at atmospheric pressure. A preferred set of conditions are about 87°C. with a residence time of about 2 hours. This temperature may be raised or lowered so long as the residence time is adjusted to leave 10–15% of the formaldehyde available for the distillation column reactor. The overall flow from this back mix reactor is added to the top stage of a 30-plate distillation column being operated at atmospheric pressure, a base temperature of 105°C., a top temperature at 85°C. and under total reflux. The total contact time on each stage is about 10 seconds. In this column the remaining hydroxypivaldehyde is converted to neopentyl glycol. In the base of the distillation column all excess formaldehyde is consumed. Residence time in the base is one-half to 1 hour.

The desirability of using stoichiometric equivalents as opposed to the previously known processes wherein a significant excess of formaldehyde is used lies in the fact that to produce specification grade neopentyl glycol a minimum of higher esters must be present. To accomplish this the final hydroxypivaldehyde and formaldehyde content of the unrefined neopentyl glycol must be below about 0.1% so that the neopentyl glycol to hydroxypivaldehyde ratio is at least 99.5:1. Further benefit is derived from this in that by reducing the amount of hydroxypivaldehyde going to higher esters the yields and economics of the process are significantly improved. It has been found that no more than about a 10% excess of formaldehyde is required using this process. That is for a feed aldehyde having from one to three hydrogen atoms on the alpha-carbon wherein $n$ represents the number of hydrogens on the alpha-carbon. The required amount of formaldehyde will lay in the range of from $(n + 1)$ moles formaldehyde per mole of feed aldehyde to $(n + 1)(1.1)$ moles of formaldehyde per mole of feed aldehyde (i.e., from about the stoichiometric amount of formaldehyde to about 10% formaldehyde above the stoichiometric amount). If greater amounts of formaldehyde are used the excess formaldehyde is consumed in the base of the distillation column and goes to produce sugars. A minimum amount of about 0.55 moles of sodium carbonate per mole of higher aldehyde are required. Greater amounts can be used if desired. However, no advantage is obtained and the excess sodium carbonate may enter into side reactions with the aldehydes to form organic sodium compounds which present increased purification problems and represent a loss of available sodium carbonate.

The novelty of using the distillation column for the second stage reactor is further emphasized by an experiment wherein the distillation column is replaced by three stirred vessels in which the total residence time is 6 hours. The vessels are operated at 90°C. with the vacuum adjusted so that the solution boils. This reactor scheme fails to achieve the desired complete conversions and cannot be operated continuously because of the dark colored materials which build up in the final two stages.

It is also quite surprising that with the elevated temperatures used formaldehyde does not react with sodium carbonate according to the following reaction:

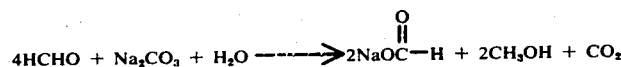

The polyhydric alcohols produced by this process are known chemicals with known utilities in applications such as polyesters, synthetic lubricants, alkyds, plasticizers, etc.

The process of this invention is further illustrated by the following examples. It will be understood, however, that these examples are not intended to limit the invention in any way and obvious modifications will appear to those skilled in the art.

EXAMPLE 1

Neopentyl glycol is prepared in a batch operation using only isobutyraldehyde, formaldehyde, and sodium carbonate. A mixture composed of 6 moles of formaldehyde as 37 percent formalin, 3 moles of isobutyraldehyde, and 1.55 moles of sodium carbonate (2.0 molar aqueous solution) is heated to reflux for 3 hours in a stirred reactor. Near the end of this time the reaction mixture turns very dark and no formaldehyde or hydroxypivaldehyde can be detected. The yield of neopentyl glycol is 82.5 percent of theoretical.

EXAMPLE 2

In this example a conventional staged system is used in an attempt to produce specification grade neopentyl glycol. The isobutyraldehyde/formaldehyde/sodium carbonate in mole ratios of 1.0/2.07/0.64 is fed to the first stage which is a recirculating stirred reactor. The reaction mixture from Stage 1 is fed to a series of three more stirred reaction vessels for a total residence time in all four stages of 8 hours. Six and three-tenths percent sodium hydroxide is added to the final stage in an attempt to achieve complete conversion. The temperature in each stage is 90° ± 4°C. The yield (based on isobutyraldehyde) to neopentyl glycol is 96.2 percent and to hydroxypivaldehyde is 2.9 percent for the first 8 hours of operation. The isolated product contains 1.9 percent ester as hydroxypivalyl hydroxypivalate. After the first 8 hours the conversion of hydroxypivaldehyde drops rapidly due to the formation of the dark color and the run has to be terminated. The final three stages are operated under a vacuum so that they will boil to help remove carbon dioxide.

EXAMPLE 3

In this example isobutyraldehyde/formaldehyde/sodium carbonate in the mole ratio of 1.0/2.01/0.53 is fed to the first stage of the reactor system used in Example 2. Total residence time in Stage 1 is 2 hours at 87°C. The material is then fed onto the top stage of a 30-plate distillation column operated at atmospheric pressure and with a base temperature of 105°C. and a top temperature of 85°C. The material has an average residence time on each plate of 10 seconds. The residence time in the base of the column is unimportant so long as the base is vigorously boiling. The neopentyl glycol produced in this manner contains less than 0.3 percent ester. Commercial specifications for neopentyl glycol call for not more than 0.5 percent ester. The yield of neopentyl glycol based on isobutyraldehyde is 98.7 percent. The reaction is stable and can be operated continuously (i.e. for several days) without apparent deterioration in product yield.

EXAMPLE 4

This example illustrates the formation of other polyhydric alcohols. A mixture consisting of 1.5 moles of n-butyraldehyde and 5.25 moles of formaldehyde as 37 percent formalin is prepared in a stirred reactor vessel. A 2.1 molar solution of sodium carbonate in water is added slowly until 110 milliliters have been added at 50°C. The mixture is raised to a higher temperature and is boiled while the remaining sodium carbonate (335 milliliters) is added. The mole ratio of n-butyraldehyde to formaldehyde to sodium carbonate is 1.0/3.5/0.60.

The yield of trimethylolpropane product is 130 grams or 64.6 percent of theoretical based on the original n-butyraldehyde.

EXAMPLE 5 n-Butyraldehyde, formaldehyde, and sodium carbonate in the mole ratio of 1.0/3.2/1.0 are fed continuously to a reactor as in Example 2. The reactor is operated at 60°C. The material overflows to a small hold tank maintained at 60°C. The total residence time is 2 hours. The overflowing material is pumped to the top of a 2-inch by 30-plate distillation column operated at atmospheric pressure, a top temperature of 91°C. and with boiling occuring in the base.

The yield to trimethylolpropane measured by gas chromatography is 83.5 percent based on n-butyraldehyde added. An additional 8.6 percent is converted to 2-ethylacrolein.

Although the invention has been described in considerable detail with particular reference to certain preferred embodiments thereof, variations and modifications can be effected within the spirit and scope of the invention as described hereinabove and as defined in the appended claims.

We claim:

1. A process for the manufacture of polyhydric alcohols by the aldol condensation of formaldehyde with a second aldehyde having the formula $R_{3-n}H_nC—CHO$ wherein $n$ is an integer of 1 to 3 inclusive and R is alkyl of 1 to 6 carbons in an aqueous medium in the presence of a sodium carbonate condensing agent which comprises the steps of (1) introducing the aldehydes in the ratio of from about $(n+1)$ to about $(1.1)(n+1)$ moles of formaldehyde per mole of second aldehyde and said sodium carbonate condensing agent into a stirred back mix reactor or a plurality of said reactors connected in series through which the reaction mixture is passed while being subject to back mixing until from about 85 to about 90 percent of the available formaldehyde is reacted and (2) withdrawing the said reaction mixture from the continuously stirred back mix reactor or reactors and introducing said reaction mixture near the top of a distillation column operated under substantially total reflux wherein the reaction mixture passes downwardly through the column and any remaining aldol condensation product is converted to the desired polyhydric alcohol.

2. A process as in claim 1 wherein the temperature of the reaction mixture in the first reaction vessel is from about 50°C. to about 110°C. at atmospheric pressure.

3. A process as in claim 1 wherein the feed materials are continuously introduced into the stirred back mix reactor and a formaldehyde-free product stream is continuously withdrawn from the base of the said distillation column.

4. A process as in claim 1 wherein the second aldehyde utilized is isobutyraldehyde and the product polyhydric alcohol is neopentyl glycol.

5. A process as in claim 1 wherein the second aldehyde fed is n-butyraldehyde and the product polyhydric alcohol is trimethylolpropane.

6. A process as in claim 1 wherein the second aldehyde fed is propionaldehyde and the product polyhydric alcohol is trimethylolethane.

7. A process as in claim 1 wherein the second aldehyde fed is acetaldehyde and the product polyhydric alcohol is pentaerythritol.

8. A process as in claim 3 wherein the second aldehyde utilized is isobutyraldehyde and the product polyhydric alcohol is neopentyl glycol.

9. A process as in claim 3 wherein the second aldehyde fed is n-butyraldehyde and the product polyhydric alcohol is trimethylolpropane.

10. A process as in claim 3 wherein the second aldehyde fed is propionaldehyde and the product polyhydric alcohol is trimethylolethane.

11. A process as in claim 3 wherein the second aldehyde fed is acetaldehyde and the product polyhedric alcohol is pentaerythritol.

* * * * *